United States Patent
Fu et al.

(10) Patent No.: US 11,369,629 B2
(45) Date of Patent: Jun. 28, 2022

(54) ENZYMATIC PREPARATION OF INCREASED ANTICOAGULANT BOVINE SOURCED HEPARIN

(71) Applicant: RENSSELAER POLYTECHNIC INSTITUTE, Troy, NY (US)

(72) Inventors: Li Fu, Troy, NY (US); Kevin Li, Middletown, NY (US); Daisuke Mori, Rensselaer, NY (US); Makoto Hirakane, Rensselaer, NY (US); Jonathan S. Dordick, Schenectady, NY (US); Robert J. Linhardt, Albany, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 17/093,953

(22) Filed: Nov. 10, 2020

(65) Prior Publication Data

US 2021/0113607 A1    Apr. 22, 2021

Related U.S. Application Data

(63) Continuation of application No. 16/496,149, filed as application No. PCT/US2018/023394 on Mar. 20, 2018, now Pat. No. 10,864,227.

(60) Provisional application No. 62/473,606, filed on Mar. 20, 2017.

(51) Int. Cl.
*A61K 31/727* (2006.01)
*C12N 9/10* (2006.01)
*C12P 19/26* (2006.01)

(52) U.S. Cl.
CPC .............. *A61K 31/727* (2013.01); *C12N 9/13* (2013.01); *C12P 19/26* (2013.01)

(58) Field of Classification Search
None
See application file for complete search history.

(56) References Cited

U.S. PATENT DOCUMENTS 8,067,196 B2 * 11/2011 Rosenberg .............. C12P 19/26
435/68.1

OTHER PUBLICATIONS

CN 102911981A, Feb. 6, 2013, machine translation. (Year: 2013).*
Tovar, BMC Research Notes 2013; 6:230. (Year: 2013).*

* cited by examiner

*Primary Examiner* — Layla D Berry
(74) *Attorney, Agent, or Firm* — Murtha Cullina LLP; Anthony P. Gangemi (57) ABSTRACT

A heparin structure with increased anticoagulant activity and method of making the same are disclosed. A heparin sample is provided and treated with a heparan sulfate sulfotransferase in an enzymatic reaction to add sulfuryl groups from a sulfuryl group source to the heparin sample, resulting in a heparin structure having above about 8% more 3-O-sulfo groups relative to wild-type bovine intestinal heparin. The added sulfuryl groups modify the heparin structure and increase the sample's binding to antithrombin III and its anticoagulant activity to be more similar and a viable alternative to porcine intestinal heparin. The modified heparin exhibits an anti-FXa activity and an anti-FIIa activity greater than about 180 U/mg, and a ratio of the anti-FXa activity to the anti-FIIa activity of about 0.9 to about 1.1, consistent with U.S. Pharmacopeia (USP) heparin activity specifications.

17 Claims, 6 Drawing Sheets

| heparin | disaccharide composition (mol %) | | | | | | | | sulfo groups per disaccharide | Mw | activity (U/mg) | | |
|---|---|---|---|---|---|---|---|---|---|---|---|---|---|
| | 0S | NS | 6S | 2S | NS6S | NS2S | 2S6S | TriS | | | anti-Xa | anti-IIa | Xa/IIa |
| USP specs | | | | | | | | | 2.5~2.7 | 15000~19000 | | >180 | 0.9~1.1 |
| BI (USP) heparin | 4.0 | 3.2 | 3.7 | 2.0 | 10.2 | 7.8 | 1.5 | 67.7 | 2.5 | 17000 | 200 | 200 | 1.0 |
| BI heparin 3S | 3.3 | 5.9 | 0.8 | 2.5 | 8.2 | 32.2 | 0.2 | 46.8 | 2.3 | 18500 | 180 | 185 | 1.0 |
| BI heparin 3SS | 3.9 | 6.3 | 0.0 | 2.5 | 5.7 | 32.1 | 0.0 | 49.5 | 2.3 | 18500 | 231 | 260 | 0.9 |
| BI heparin 3SSG | 3.6 | 5.4 | 0.0 | 2.4 | 6.1 | 15.3 | 0.0 | 67.2 | 2.5 | 17900 | 289 | 301 | 1.0 |

ENZYMATIC PREPARATION OF INCREASED ANTICOAGULANT BOVINE SOURCED HEPARIN

CROSS REFERENCE TO RELATED APPLICATION(S)

This application is a continuation of U.S. Utility patent application Ser. No. 16/496,149, filed Sep. 20, 2019, which is a National Stage filing of International Application No. PCT/US2018/023394, filed Mar. 20, 2018, which claims priority to U.S. Provisional Patent Application No. 62/473,606 entitled "Enzymatic Preparation of Anticoagulant Bovine Sourced Heparin" filed on Mar. 20, 2017, which is incorporated by reference in its entirety.

BACKGROUND

This disclosure is directed to methods of increasing anticoagulant activity of heparin, and more particularly to a process for preparing heparin for use as an anticoagulation medication.

Heparin is a naturally occurring anticoagulant produced by white blood cells and can be used therapeutically in human and veterinary patients to prevent the formation of blood clots and/or the extension of existing clots within the blood. Currently, heparin is mainly sourced from porcine intestine mucosa in China.

Given increasing worldwide demand for heparin, a potential shortage has led to a push for the re-introduction of bovine heparin to increase the supply. However, compared to porcine heparin, bovine heparin has relatively low anticoagulant activity, which does not meet current U.S. Pharmacopeia (USP) heparin activity specifications.

To address the growing demand for heparin, what is needed is an alternative source of therapeutically effective heparin that can be safely, simply and easily produced. The instant disclosure is believed to address this need.

SUMMARY

Some embodiments of the disclosed subject matter are directed to a method of increasing anticoagulant activity of a heparin sample. The heparin sample is provided to and treated with a concentration of heparan sulfate sulfotransferase in an enzymatic reaction to add sulfuryl groups from a sulfuryl group source to the heparin sample. In some embodiments, this treatment occurs within a reaction medium that includes a sulfuryl group source, a sulfuryl group regeneration source, a sulfuryl group regeneration enzyme, or combinations thereof. The modified heparin structure with added sulfuryl groups exhibit increased binding to antithrombin III and anticoagulant activity, and is similar in structure and activity to porcine intestinal heparin. In some embodiments, the heparin sample to be modified includes bovine intestinal heparin, bovine lung heparin, bovine mucosa heparin, ovine intestinal heparin, porcine derived heparin, or combinations thereof.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DETAILED DESCRIPTION

Figure 1:
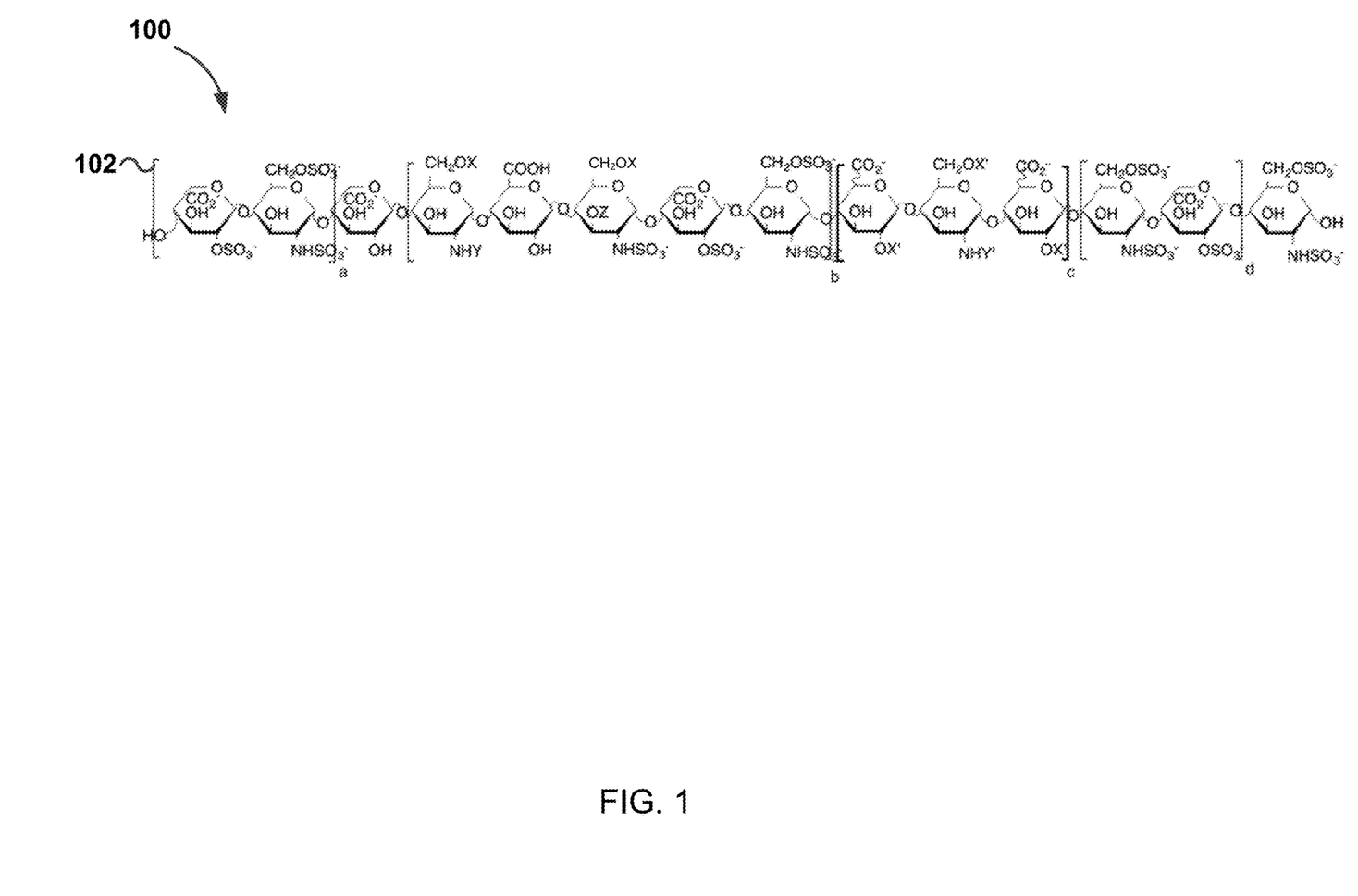
FIG. 1 is a schematic drawing of a heparin structure according to some embodiments of the disclosed subject matter.

Referring now to FIG. 1, aspects of the disclosed subject matter include a heparin 100. In some embodiments, heparin 100 is a modified form of a corresponding wild-type or substantially wild-type heparin polysaccharide or heparin extracted from an animal tissue or cultured animal or human cells. As a result of this modification, which will be discussed in greater detail below, heparin 100 exhibits increased anticoagulation activity compared with the corresponding wild-type or substantially wild-type heparin polysaccharide. Additionally, as a result of this modification, heparin 100 has increased structural similarity to porcine (pig) intestinal heparin. In some embodiments, heparin 100 is modified from bovine (cattle) derived heparin or ovine (sheep) derived heparin. In some embodiments, heparin 100 is modified from bovine intestinal heparin, bovine lung heparin, bovine mucosa heparin, or ovine intestinal heparin. In some embodiments, heparin 100 is modified from porcine derived heparin, e.g., those porcine heparins having lower anticoagulation activities than pharmaceutical grade porcine intestinal heparin.

The heparin 100 includes heparin structure 102. In some embodiments of heparin structure 102, a+d is about 14 to about 18. In some embodiments, of heparin structure 102, b is 1 to 3. In some embodiments, of heparin structure 102, b is 2. In some embodiments of heparin structure 102, c is about 2 to about 8.

In some embodiments of heparin structure 102, X and X' are $SO_3^-$, H, or combinations thereof. In some embodiments, X and X' in b and c is about 4H and/or about 4 $SO_3^-$. In some embodiments of heparin structure 102, Y and Y' are $SO_3^-$, $COCH_3$, H, or combinations thereof. In some embodiments, Y and Y' in b and c is about 6 $SO_3^-$, about 1 $COCH_3$, and/or about 1H. In some embodiments of heparin structure 102, Z is $SO_3^-$, H, or combinations thereof. In some embodiments, Z is about 0.8 $SO_3^-$ and about 0.2H.

As will be discussed in great detail below, and without wishing to be bound by theory, one of the structural differences between heparin 100 and the corresponding wild-type or substantially wild-type heparin is an increase of 3-O-sulfo groups and/or 6-O-sulfo groups. In some embodiments, heparin 100 includes above about 8% more 3-O-sulfo groups relative to wild-type bovine intestinal heparin. In some embodiments, heparin 100 includes about 15% to about 25% more 6-O-sulfo groups and about 8% to about 20% more 3-O-sulfo groups relative to wild-type bovine intestinal heparin.

Figure 2A:
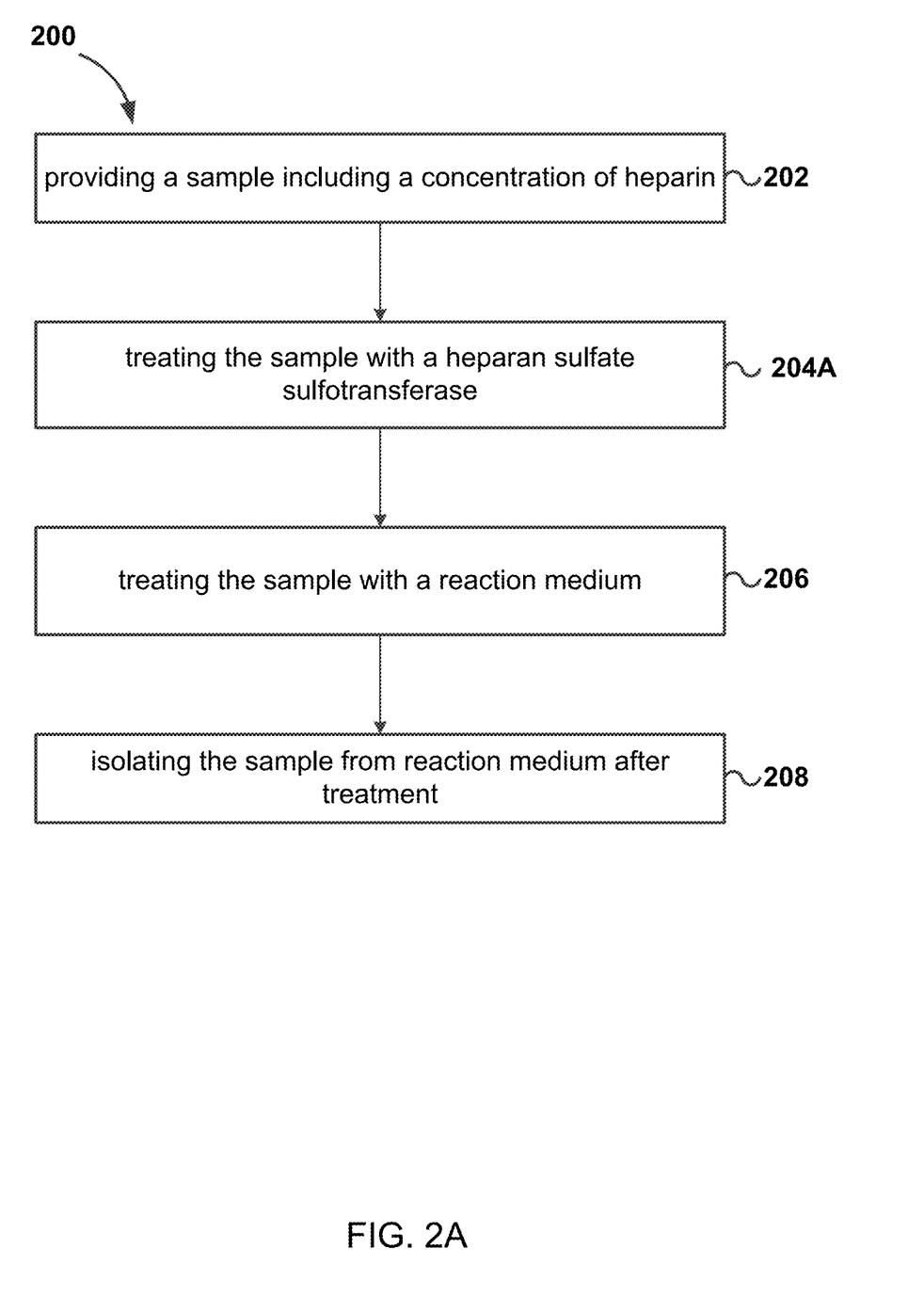
FIG. 2A is a chart of a method for increasing anticoagulant activity of bovine heparin according to some embodiments of the disclosed subject matter.
Figure 2B:
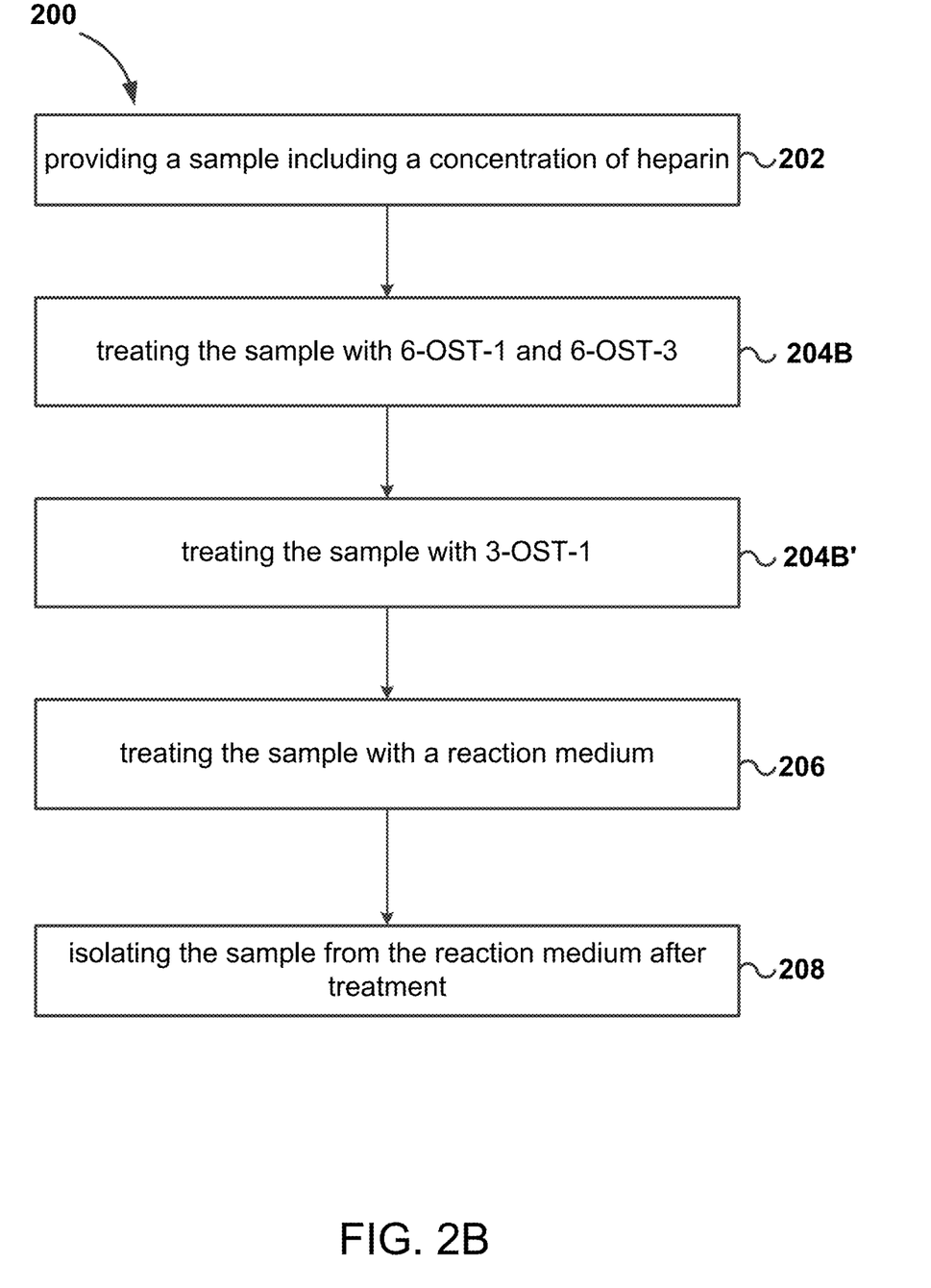
FIG. 2B is a chart of a method for increasing anticoagulant activity of bovine heparin according to some embodiments of the disclosed subject matter.

Referring now to FIG. 2A, aspects of the disclosed subject matter include a method 200 of increasing anticoagulant activity of heparin. At 202, a sample including a concentration of heparin is provided. As discussed above, in some embodiments, the concentration of heparin is bovine derived heparin, ovine derived heparin, porcine derived heparin, etc., or combinations thereof. At 204A, the sample is treated with a heparan sulfate sulfotransferase. In some embodiments, heparan sulfate sulfotransferase includes a 6-O-sulfotransferase (6-OST-X), 3-O-sulfotransferase (3-OST-X), or combinations thereof. In some embodiments, heparan sulfate sulfotransferase includes 6-OST-1, 6-OST-3, 3-OST-1, or combinations thereof. In some embodiments, heparan sulfate sulfotransferase includes 6-OST-1, 6-OST-3, and 3-OST-1. Referring now to FIG. 2B, in some embodiments, the sample is treated at 204B with 6-OST-1 and 6-OST-3 before being treated at 2043 with 3-OST-1.

Referring again to FIG. 2A, at 206, the sample is treated with a reaction medium. In some embodiments, the reaction medium includes a sulfuryl group source to facilitate sulfurylization of the heparin sample by the heparan sulfate sulfotransferase. In some embodiments, the sulfuryl group source includes 3'-phosphoadenosine-5'-phosphosulfate (PAPS), PAPS derivatives, PAPS analogs, or combinations thereof. In some embodiments, the reaction medium includes a sulfuryl group recycle system. In some embodiments, the sulfuryl group recycle system includes a sulfuryl group regeneration source, a sulfuryl group regeneration enzyme, or combinations thereof. In some embodiments, the sulfuryl group regeneration source includes p-nitrophenyl sulfate (PNPS), PNPS derivatives, PNPS analogs, or combinations thereof. In some embodiments, the sulfuryl group regeneration enzyme includes arylsulfotransferase-IV (AST-IV), other aryl sulfotransferase or mutants of AST-IV capable of recycling, or combinations thereof. In some embodiments, the reaction medium further comprises a buffer. In some embodiments, the buffer has a pH of about 7.1 to about 7.3. In some embodiments, the buffer is 2-(N-morpholino) ethanesulfonic acid (MES).

At 208, the treated sample is isolated or purified after treatment. Any suitable purification process known to those having skill in the art can be used, e.g., filtration, chromatography, centrifugation, etc., or combinations thereof. In some embodiments, the heparin sample exhibits an anti-FXa activity and an anti-FIIa activity greater than about 180 U/mg. In some embodiments, the ratio of the anti-FXa activity to the anti-FIIa activity of the heparin sample is about 0.9 to about 1.1. In some embodiments, method 200 includes one or more post processing steps (not shown). The one or more post processing steps include any process to better prepare heparin 100 for packaging or use as an anticoagulant in treatment of a patient, e.g., lyophilization, resuspension, etc., or combinations thereof. In some embodiments, heparin 100 is produced by one or more steps of method 200, including treatment with a heparan sulfate sulfotransferase, treatment with a reaction medium, treatment with a reaction medium including a sulfuryl group recycle system, isolating the treated sample, or combinations thereof. In some embodiments, the PAPS is generated in situ or regenerated from 3'-phosphoadenosine 5'-phosphate (PAP) in situ.

Figure 3:
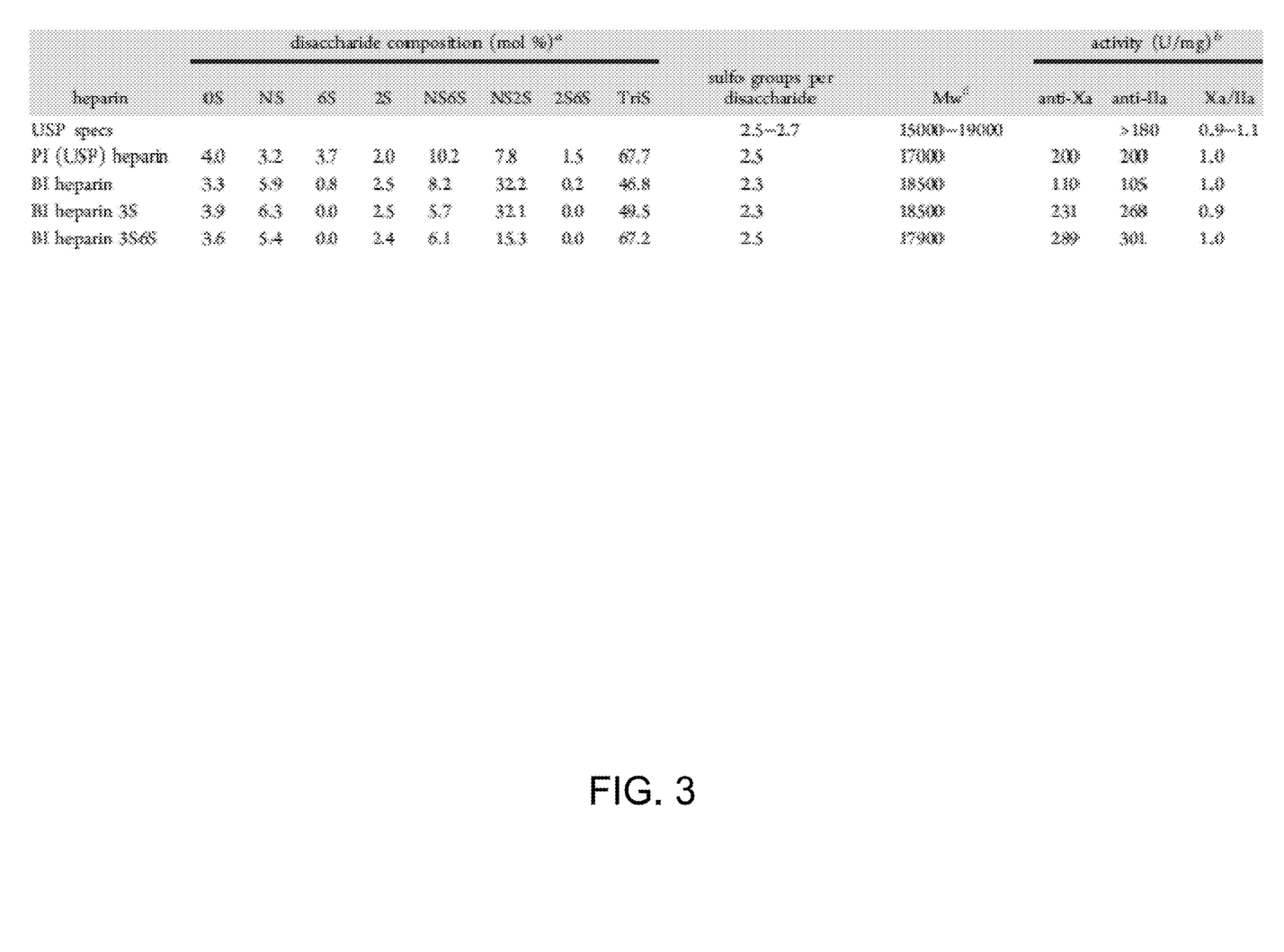
FIG. 3 is a disaccharide composition table heparin structures according to some embodiments of the disclosed subject matter.

As discussed above, due to structural differences which limit activity of other heparins in comparison with porcine intestinal heparin, other heparins (such as bovine intestinal heparin) require as much as a 3-fold concentration increase over porcine intestinal heparin to meet USP activity standards. The methods of the present disclosure are beneficial in that they modify heparins exhibiting decreased anticoagulant activity, e.g., bovine heparins, ovine heparins, etc., to have a structure more similar to that of porcine intestinal heparin. As shown in FIG. 3, and without wishing to be bound by theory, the modified heparins have similar disaccharide composition to porcine intestinal heparin, and further increased 3-O-sulfo containing residues for heparin binding to antithrombin III and its anticoagulant activity. As a result, as discussed above and shown in the Example below, heparin 100 exhibits similar anti-FXa and an anti-FIIa activity to porcine intestinal heparin, and the enhanced anticoagulant activities of bovine heparins prepared using this simplified enzymatic synthesis meet USP heparin activity specifications. Finally, the method of modification is not complicated or resource intensive, meaning that the increasing demands for therapeutically effective heparin can be met without burdensome expense.

EXAMPLE

Two bovine intestinal (BI) heparin samples (20 mg each) were treated in parallel either with 6-OST-1, 6-OST-3 and 3-OST-1, or with only 3-OST-1. The sulfation reaction was coupled with a PAPS recycling system that consisted of PNPS, PAPS, and AST-IV. The reaction conditions were as follows: substrate concentration of 1 mg/mL, each enzyme concentration of 0.5 mg/mL for 50% slurry, PNPS and PAPS concentrations of 10 mM and 250 μM, respectively. The reactions were incubated at 37° C. for 40 h in 50 mM MES buffer (pH 7.2). After the reaction was complete, the mixtures were filtered to remove enzyme resin and dialyzed using 5K Da molecular weight cutoff (MWCO) centrifugal membrane units with distilled water to remove PNP, PAPS, MES salt, and other small molecule impurities. The retentates were lyophilized for further analysis.

Figure 4A:
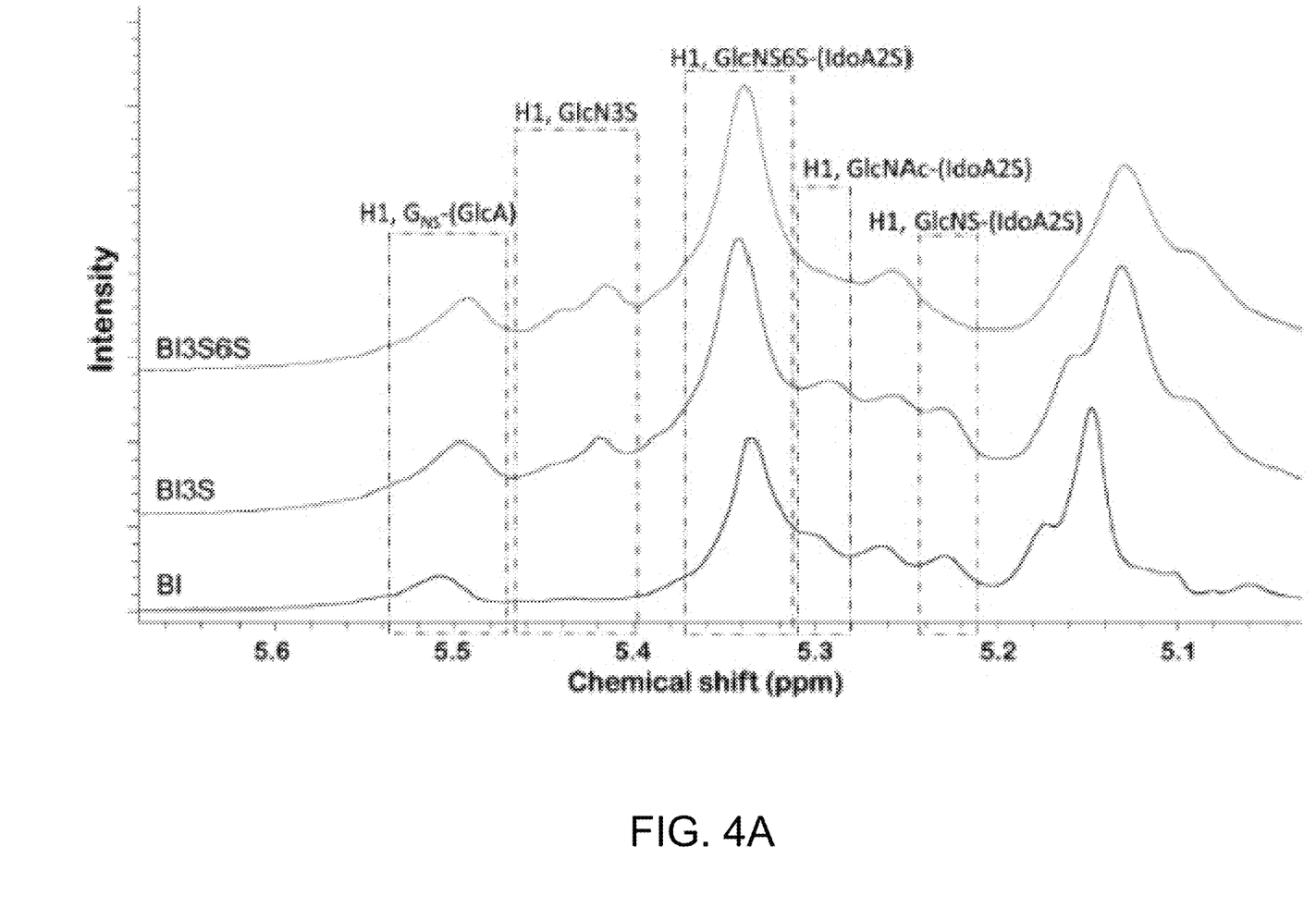
FIG. 4A is a nuclear magnetic resonance (NMR) spectrum of a heparin structure according to some embodiments of the disclosed subject matter.
Figure 4B:
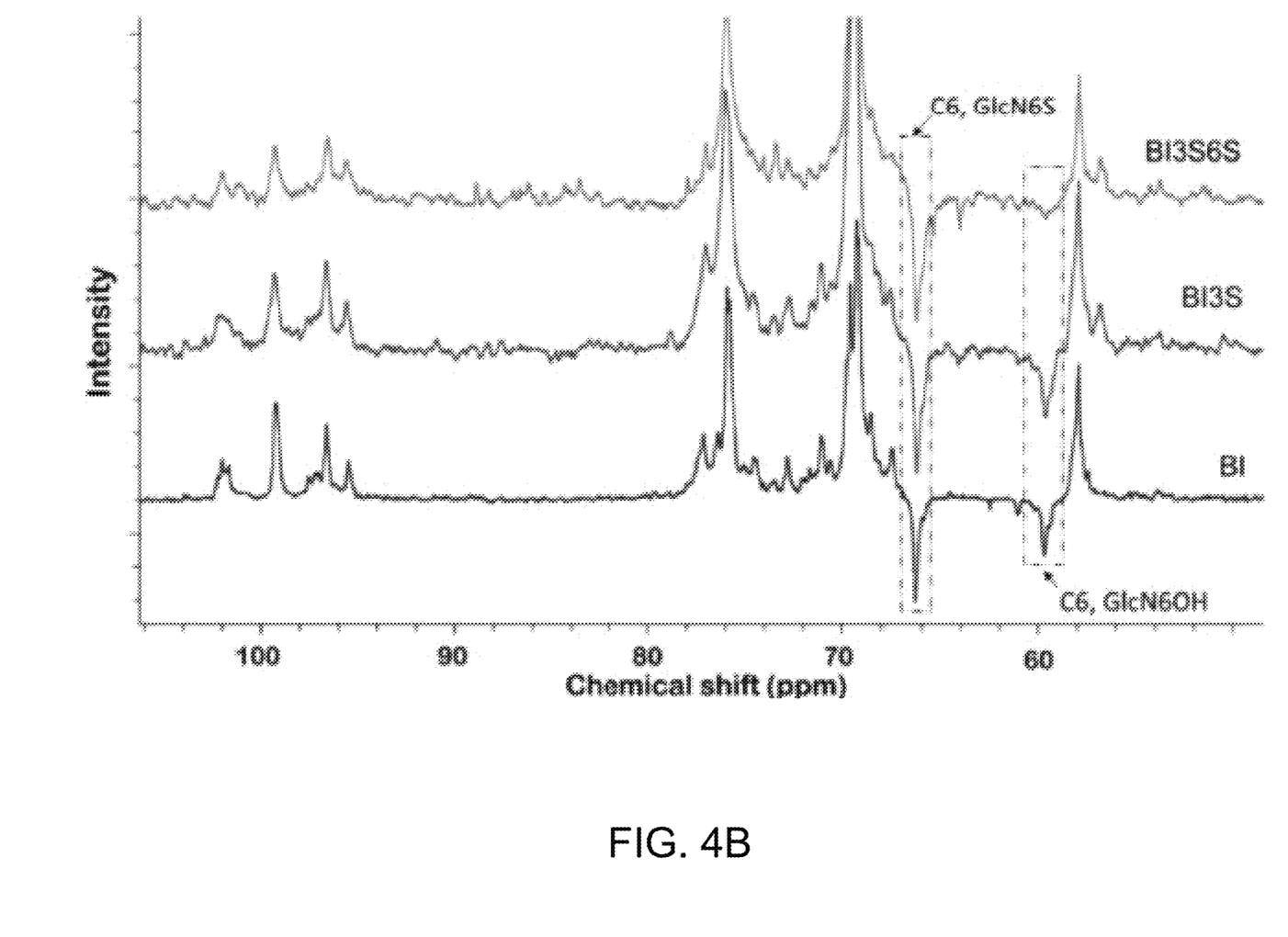
FIG. 4B is a nuclear magnetic resonance (NMR) spectrum of a heparin structure according to some embodiments of the disclosed subject matter.

NMR and disaccharide compositional analysis confirmed the purity of each polysaccharide product to be >95%. The anomeric signals in the partial 1H NMR spectrum shown in FIG. 4A were assigned and integrated. Treatment of BI heparin with 6-OST-1, 6-OST-3, and 3-OST-1 increased the content of 6-O-sulfo and 3-O-sulfo groups therein (62-81% and 5-19%, respectively). While the increase in 3-O-sulfo groups in both enzyme treated BI heparins were demonstrated, it was more difficult to demonstrate the increase in 6-O-sulfo groups because of the structural heterogeneity of these polysaccharides. To that end, 1D distortionless enhancement by polarization transfer (DEPT)-135 13C NMR spectra were obtained to examine definitively the change in 6-O-sulfo group content of the BI heparin treated with 6-OST-1, 6-OST-3, and 3-OST-1 (FIG. 4B). DEPT spectroscopy resulted in a negative signal for the primary C6 carbon allowing the clear assignment of the C6 of N,6-O-sulfo glucosamine (GlcNS6S) and N-sulfated glucosamine (GlcNS) resonances. These experiments confirmed that only the sample treated with 6-OST-1 and 6-OST-3 showed increased GlcNS6S content and decreased GlcNS content.

The anticoagulant activity of the modified bovine intestinal heparins was measured using the methods described in the USP heparin monograph and compared to those of porcine intestinal (PI) and BI heparins (FIG. 3). PI heparin showed an anti-FXa activity of 200 U/mg, an anti-FIIa activity of 200 U/mg, and an anti-FXa/anti-FIIa ratio of 1.0, consistent with USP requirements of >180 U/mg with an anti-FXa/anti-FIIa ratio of 0.9-1.1. BI heparin showed considerably lower anti-FXa activity of 110 U/mg, an anti-FIIa activity of 105 U/mg with an anti-FXa/anti-FIIa ratio of 1.0. BI3S and BI3S6S heparins both showed activities greatly enhanced over PI heparin. Although remodeled BI heparin shows relatively higher anticoagulant activity, it meets all current USP criteria for pharmaceutical grade heparin. Without wishing to be bound by theory, the anticoagulant activities of a given heparin structure sample can be increased to meet current USP specifications or even higher future standard specifications, e.g., controlling catalyst addition, reaction time, etc., or combinations thereof.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A method of increasing anticoagulant activity of heparin comprising:
   providing a sample including a concentration of heparin; and
   treating the sample with a heparan sulfate sulfotransferase,
   thereby increasing the anticoagulation activity of the heparin in the sample,
   wherein the heparan sulfate sulfotransferase is 6-OST-1, 6-OST-3, and 3-OST-1.

2. The method according to claim 1, further comprising treating the sample with a reaction medium including a sulfuryl group source.

3. The method according to claim 2, wherein the reaction medium further comprises a sulfuryl group regeneration source, a sulfuryl group regeneration enzyme, or combinations thereof.

4. The method according to claim 1, wherein the heparin is a bovine derived heparin, ovine derived heparin, porcine derived heparin, or combinations thereof.

5. The method according to claim 4, wherein the heparin is bovine intestinal heparin, bovine lung heparin, bovine mucosa heparin, ovine intestinal heparin, or combinations thereof.

6. The method according to claim 1, wherein the sample is treated with 6-OST-1 and 6-OST-3 before being treated with 3-OST-1.

7. The method according to claim 2, wherein the sulfuryl group source is 3'-phosphoadenosine-5'-phosphosulfate (PAPS); the sulfuryl group regeneration enzyme is arylsulfotransferase-IV (AST-IV); and the sulfuryl group regeneration source is p-nitrophenyl sulfate (PNPS).

8. The method according to claim 2, wherein the reaction medium further comprises 2-(N-morpholino) ethanesulfonic acid (MES) having a pH of about 7.1 to about 7.3.

9. The method according to claim 2, further comprising:
   isolating the sample from the heparan sulfate sulfotransferase and the reaction medium after treatment.

10. The method according to claim 4, wherein the treated heparin comprises the structure:

wherein:
   a+d is about 14 to about 18;
   b is 2;
   c is about 2 to about 8;
   X and X' are $SO_3^-$, H, or combinations thereof;
   Y and Y' are $SO_3^-$, COCH3, H, or combinations thereof; and
   Z is $SO_3^-$, H, or combinations thereof.

11. The method according to claim 10, wherein X and X' in b and c is about 4 H or about 4 $SO_3^-$.

12. The method according to claim 10, wherein Y and Y' in b and c is about 6 $SO_3^-$, about 1 $COCH_3$, and about 1 H.

13. The method according to claim 10, wherein Z is about 0.8 $SO_3^-$ and about 0.2 H.

14. The method according to claim 10, wherein the heparin structure includes above about 8% more 3-O-sulfo groups relative to wild-type bovine intestinal heparin.

15. The method according to claim 14, wherein the heparin structure includes about 15% to about 25% more 6-O-sulfo groups and about 8% to about 20% more 3-O-sulfo groups relative to wild-type bovine intestinal heparin.

16. The method according to claim 10, wherein the heparin structure includes an anti-FXa activity and an anti-FIIa activity greater than about 180 U/mg, and the ratio of the anti-FXa activity to the anti-FIIa activity is about 0.9 to about 1.1.

17. A method of increasing anticoagulant activity of bovine heparin comprising:
   providing a sample including a concentration of bovine heparin;
   treating the sample with a heparan sulfate sulfotransferase; and
   treating the sample with a reaction medium including a sulfuryl group source, a sulfuryl group regeneration source, a sulfuryl group regeneration enzyme, or combinations thereof,
   thereby increasing the anticoagulation activity of the bovine heparin, wherein the treated bovine heparin includes:

wherein:
- a+d is about 14 to about 18;
- b is 2;
- c is about 2 to about 8;
- X and X' are $SO_3^-$, H, or combinations thereof;
- Y and Y' are $SO_3^-$, COCH3, H, or combinations thereof; and
- Z is $SO_3^-$, H, or combinations thereof, and wherein the heparan sulfate sulfotransferase is 6-OST-1, 6-OST-3, and 3-OST-1.

* * * * *